United States Patent [19]

Heine

[11] 3,934,578
[45] Jan. 27, 1976

[54] DIRECT ILLUMINATION OTOSCOPE
[75] Inventor: Helmut A. Heine, Herrsching, Germany
[73] Assignees: Propper Manufacturing Co., Inc., Long Island, N.Y.; Optotechnik Heine KG, Herrsching, Germany; part interest to each
[22] Filed: May 28, 1974
[21] Appl. No.: 473,499

[52] U.S. Cl. ................ 128/9; 313/318; 339/176 L; 240/218
[51] Int. Cl.² .......................................... A61B 1/06
[58] Field of Search .......... 128/4, 6, 9, 18; 313/318; 339/353 R, 176 L, 177, 182 L, 183; 240/18, 217, 218

[56] References Cited
UNITED STATES PATENTS

| | | | |
|---|---|---|---|
| 819,624 | 5/1906 | Wood | 339/182 L |
| 2,066,328 | 1/1937 | Cameron | 128/9 |
| 2,285,987 | 6/1942 | Krimsky | 240/2 M |
| 2,592,190 | 4/1952 | Rubens et al. | 240/2.18 |
| 2,683,450 | 6/1954 | Schenk | 128/9 |

*Primary Examiner*—Robert W. Michell
*Assistant Examiner*—Henry S. Layton
*Attorney, Agent, or Firm*—Amster & Rothstein

[57] ABSTRACT

The present application discloses a small size otoscope (the instrument with which the doctor examines the ear) including a bulb mounted directly in the proximal portion of the speculum body to illuminate the field of view. The bulb includes positive and negative side contacts and is adapted to be received in a sleeve positioned in the speculum, with the bulb being inserted from the rear of the sleeve to permit easy bulb replacement.

1 Claim, 5 Drawing Figures

U.S. Patent   Jan. 27, 1976   3,934,578
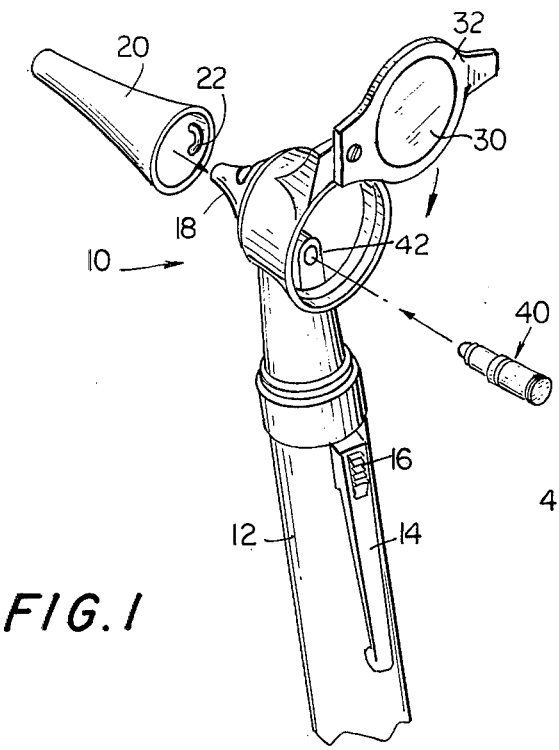
FIG. 1
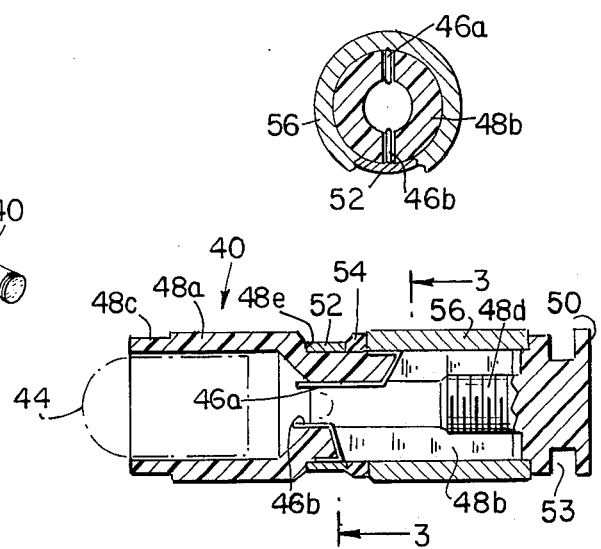
FIG. 3
FIG. 2
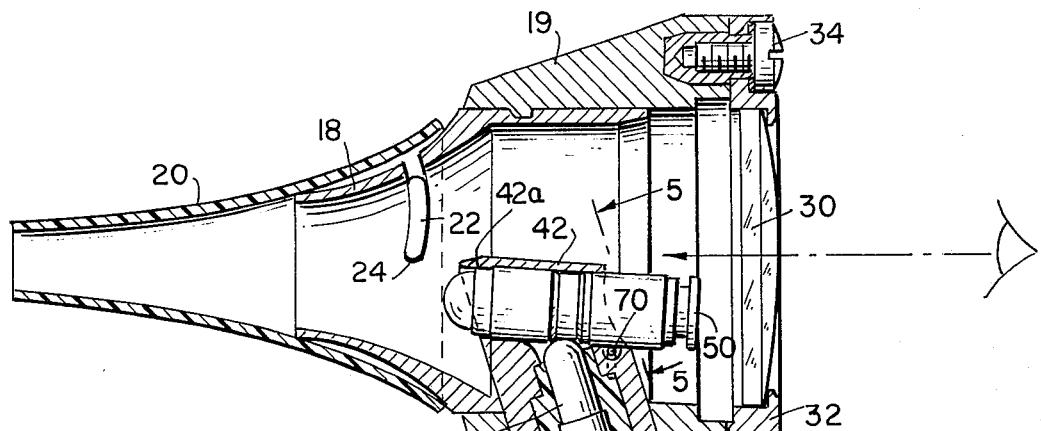
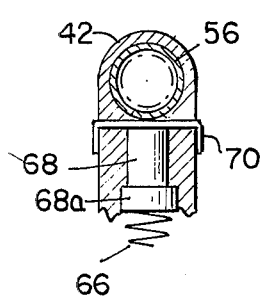
FIG. 5
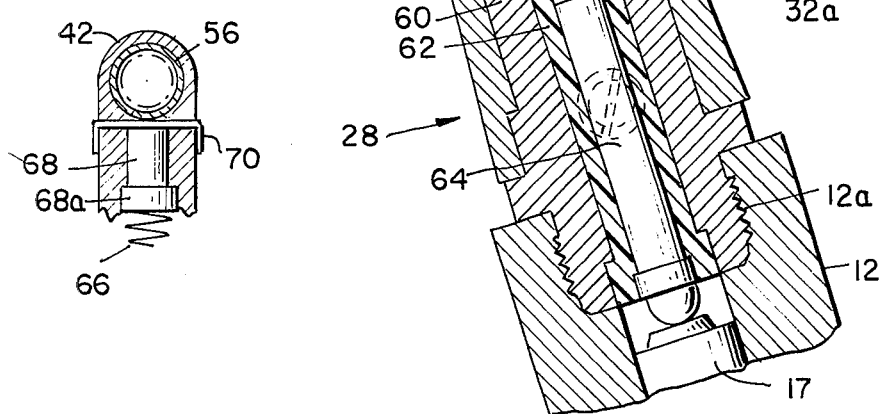
FIG. 4

DIRECT ILLUMINATION OTOSCOPE

This invention relates to medical diagnostic instruments and more specifically to an improved otoscope construction.

Routine examination of the ear, which includes examination of the outer portion of the auditory canal up to and including the tympanic membrane, is accomplished with an instrument conventionally known as an otoscope. Traditionally, this instrument includes a conical speculum which is inserted into the ear and a light source which illuminates the area at the distal end of the speculum for observation. The instrument may also include a magnifying lens at the proximal end of the speculum to magnify the field of view and a disposal speculum tip to avoid the necessity of sterilizing the instrument after each use.

The most substantial difference between the various otoscopes heretofore available resides primarily in the means by which light is provided at the distal end of the speculum. In the oldest otoscopes, a candle was used in combination with a mirror arrangement. More modern systems include an arrangement wherein a small light bulb is positioned adjacent the speculum body, with the speculum frequently being mounted on an appropriate handle either containing batteries or connected by cables to an appropriate power source. Most recently, otoscopes have been developed which include a bundle of small diameter optical fibers which are capable of transmitting light along their length in a curved path. Such fibers have been embedded within the otoscope speculum body to transmit light from a lamp usually mounted adjacent the instrument handle to the distal region of the speculum where the fibers may be formed into an annular illumination surface.

Conventional non-fiber optic otoscopes were generally relatively large to accommodate an illumination bulb mounted within or behind the speculum. The size of the distal end of the speculum is substantially determined by the conventional diameter of the auditory canal. With the bulb mounted within or behind the speculum, it was necessary to enlarge the proximal end of the speculum to permit the doctor to see over or around the bulb which partially obstructed the field of view. With the advent of optical fibers which could be embedded in the speculum itself (and therefore did not obstruct the field of view), a family of relatively small size otoscopes were developed. These otoscopes conventionally use smaller penlight batteries in a relatively small battery handle which can be clipped onto the doctor's shirt pocket to be readily available for examination. Otoscopes of this type have been found exceedingly convenient and are a valuable addition to the array of diagnostic tools available to the physician.

However, optical fibers are relatively expensive and fragile and the process of incorporating such fibers into an otoscope speculum can also be relatively costly. Under the circumstances, fiber optic otoscopes tend to be relatively more costly than conventional otoscopes of equivalent size and quality. At the same time, it has not been possible to successfully miniaturized conventional otoscope illumination arrangements because the bulb size remains relatively constant and conventional mounting arrangements would substantially obstruct the field of view in a maniaturized device. Further, the difficult of gaining access to the bulb for replacement in conventional mounting arrangements would be very much greater in a miniaturized instrument.

Accordingly, it is an object of the present invention to provide a relatively small size otoscope having a source of illumination mounted within the otoscope's speculum in which the source of illumination does not significantly obstruct the field of view and in which the source of illumination is readily accessible for easy replacement. A further object of the invention is to provide a relatively small size otoscope which does not use optical fibers.

In accomplishing these and other objects in accordance with the present invention, an otoscope includes a bulb receiving sleeve mounted in the proximal section of the otoscope speculum. A bulb having positive and negative side contact rings adapted to engage corresponding contacts within said sleeve is adapted to be inserted and removed in said sleeve from the rear thereof, adjacent to the proximal end of said speculum, to permit easy access to said bulb for replacement without obstructing the field of view.

Further objects, features and advantages of the present invention will be appreciated by reference to the attached detailed description of a presently preferred, but nonetheless representative embodiment thereof, when taken in combination with the appended drawings, wherein:

FIG. 1 is a perspective view of the otoscope with the disposable tip and illumination bulb removed;

FIG. 2 is a cross sectional view of the bulb;

FIG. 3 is a cross sectional view taken along line 3—3 in FIG. 2;

FIG. 4 is a cross sectional view of the otoscope with the disposable tip and bulb in position; and FIG. 5 is a cross sectional view taken along line 5—5 in FIG. 4.

Referring to the drawings, and particularly FIG. 1 thereof, applicant's otoscope includes an otoscope head portion 10 which is mounted on a battery carrying handle 12.

The handle is of relatively conventional design and includes a pocket clip 14 and an on-off switch 16. Handle 12 (partially shown in cross section in FIG. 4) is adapted to carry a pair of penlight batteries 17. Handle 12 includes a threaded upper portion 12a which is adapted to receive a depending threaded portion of otoscope head 10. The handle is designed such that positive contact is made from a positive terminal of battery 17 which is positioned to engage an appropriately insulated positive portion of head 10 (to be described hereinafter) while negative contact is made through the casing of handle 12 or by a strip of conductive material within the casing to the metallic body of head 10.

Otoscope head 10 itself includes a conical nose section 18 adapted to receive a disposable speculum 20. Nose section 18 may take the form of a metallic insert received within plastic speculum body section 19. Disposable speculum 20 may be of molded plastic, paper or other appropriate material and is replaced after each use of the instrument to prevent cross-infection between patients. The disposable speculum 20 includes a radial ridge 22 which is adapted to mate with a radial cut-out or slot 24 in conical nose section 18 to lock the disposable speculum on the nose section by rotation of the disposable speculum in a manner well known in the art.

Otoscope head 10 further includes a neck section 28 which mounts speculum body section 19 and is received in handle 12. The angle formed between neck section 28 and the speculum body 18 is selected so that appropriate position of a speculum can be achieved with convenient hand held position of the handle.

A lens arrangement is mounted at the proximal end of the speculum, including lens 30 mounted in lens frame 32. Frame 32 is retained by screw 34 in an upstanding ledge portion of speculum body 19 and includes a projecting tab section 32a which is positioned so that the lens frame arrangement can be conveniently pivoted into and out of position. In its upwardly pivoted position as shown in FIG. 1, the lens is completely removed from the field of view and the rear of the speculum is open. When pivoted into closed position as shown in the cross section of FIG. 4 the lens completely covers the proximal end of the speculum and seals the speculum body. The magnification of lens 30 is selected such that the focal point of the lens will be slightly beyond the distal end of the disposable tip 20 when in position.

Illumination of the distal end of the speculum is provided by bulb 40 which is adapted to be received within a bulb sleeve 42 mounted within the speculum body 19. Bulb sleeve 42 is mounted below the center of the speculum to permit observation of the field of view over and around the bulb sleeve.

Bulb 40 (best seen in FIG. 2) is adapted to have both positive and negative side contacts as opposed to the conventional side negative, rear positive arrangement usually used. To accomplish this, bulb 40 includes an evacuated bulb envelope 44 which encloses a filament (not shown) in conventional fashion and may have lens tip section to concentrate light in a forward direction in known fashion. Projecting rearwardly from bulb envelope 44 are filament legs 46a and 46b adapted to be connected across a source of electrical power to illuminate the bulb. Envelope 44 is fixed within a bulb sleeve 48 which includes a forward section 48a having a first diameter adapted to fit and receive bulb envelope 44 and a rearward section 48b having a relatively smaller diameter. The forward section 48a has a substantially constant interior diameter from its forward end to the point where the interior diameter begins to narrow into the rearward section. However, the outer diameter of the forward section is reduced adjacent its forward edge 48c to create a ledge which will be useful in positioning the bulb as described hereinafter. The rearward section 48b is slit from the rear end thereof to a point in the rear section 48b. As shown in FIG. 2, this slit is vertical with the cross section being taken in the middle of the slit. The slit in section 48b is more clearly shown in the cross sectional view of FIG. 3. The interior of the rear of section 48b is threaded at 48d to accept a screw-cap 50.

Filament legs 46a and 46b project rearwardly from bulb envelope 42 in the interior of rear section 48b and respectively bend radially outwardly through the slots to the exterior of section 48b, with leg 46b bending downwardly through the lower slot as shown in FIG. 3 and leg 46a turning upwardly through the upper slot.

A positive contact ring 52 is slipped over the rearward section 48b of the bulb chassis until it abuts against a ledge 48e in the central region of the bulb structure. Annular ring 52 is of a metallic conductive material. As will be seen in FIG. 2, the lower filament leg 46b which turns downwardly through the lower slot is bent forward on the exterior of rear section 48b and conductive ring 52 fits over leg 46b making contact with the leg. Annular ring 52 thus becomes a positive side contact terminal for the bulb.

A ring of insulating material 54 is positioned over the reduced diameter section 48b to separate the positive contact ring 52 from a negative contact ring 56 which is then positioned on the rear section 48b behind insulating ring 54. As seen in FIG. 2, filament leg 46a passes up through the upper slot and is turned back forwardly prior to the positioning of ring 56 so leg 46a makes electrical contact with ring 56 which then becomes the negative bulb contact.

As seen in FIG. 2, the outer diameter of negative bulb contact 56 is approximately equal to the outer diameter of principal forward section 48a with the outer diameter of positive contact ring 52 being slightly smaller. Further, the outer diameter of the forward section in the region immediately adjacent ledge 48e slopes radially inwardly to the right in FIG. 2 and the forward edge of ring 54 slopes radially inwardly toward the left such that the combined assembly forms an indentation in the central region of the bulb, the base of which is the positive contact ring 52.

To complete the bulb assembly, a rear screw-cap 50 having a forward projecting threaded portion is threaded into the threaded section 48d of the bulb cylinder, locking the ring assembly (including positive contact ring 52, insulating ring 54 and negative contact ring 56) on body 48. Rear cap 50 includes an annular indentation 53 around its entire circumference which permits a user to obtain a positive grasp on the bulb with a fingernail thus permitting easy removal of bulb from the bulb sleeve.

As seen in FIG. 4, the bulb sleeve 42 is merely the upper projecting portion of a unitary metallic element 60 which projects down into the interior of neck section 28. Section 60 is preferably of a conductive metallic material and its lower section is threaded to be received within the upper threaded portion 12a of handle 12. Interior of section 60 is a tubular section of insulating material 62 which extends from the lower base of the neck section to the interior of sleeve 42. Within insulating section 62 is a conductive rod 64 which at its lower end is in electrical contact with the positive terminal of battery 16. Positive contact rod 64 extends upward into neck 28 within insulating rod 62 approximately two thirds of the way up in the neck. Above rod 64 is a coil spring 66 and above spring 66 a contact stud 68 which is positioned for sliding movement within insulating rod 62. Contact stud 68 includes an oversize rear section 68a forming a ledge which is adapted to engage a ledge on the interior of insulating rod 62 such that the upwardmost position of contact stud 68 is established. Stud 68 can be depressed against the urging of spring 66.

As best seen in the cross section of FIG. 4, bulb 40 is adapted to be inserted in sleeve 42 with positive contact stud 68 running over the forward section 48a of the bulb assembly as the assembly is inserted and locking into the annular notch against positive contact ring 52. Positive contact ring 52 thus makes positive contact through stud 68, spring 66 and rod 64 with the positive battery pole. At the same time negative contact is made through negative ring 56 which engages conductive neck section 60, which is a unitary element with bulb sleeve 42. To assure negative contact, a negative spring wire element 70 may be positioned in the upper region of member 60 on the interior of sleeve 42 in position to springably abut against negative contact ring 56.

Sleeve 42 is preferably dimensioned with slightly reduced interior diameter forward section 42a adapted to receive reduced diameter outer bulb section 48c and to abut against the ledge formed thereby establishing a forwardmost position of the bulb. Obviously, this position should correspond to the position at which spring and stud 68 is seated on positive contact ring 52.

It will be appreciated that with this arrangement bulb 40 is adapted to be conveniently inserted in collar 42 in otoscope head 10 from the rear thereof and can easily be removed by grasping the ledge 53 in the bulb rear section with the fingernail. This rearward insertion arrangement permits the bulb to be easily inserted and removed without the need to gain access to the forward end of the speculum permitting the incorporation of a bulb within a relatively small size speculum suitable for a pocket instrument.

What is claimed is:

1. An otoscope comprising an otoscope speculum, a bulb sleeve within said otoscope speculum, movable contact means protruding into said sleeve, and an illumination bulb received within said sleeve from the proximal end thereof, said illumination bulb including a bulb chassis, an evacuated envelope at the forward end of said bulb chassis dimensioned to be received within said sleeve, filament contact legs extending rearwardly from said evacuated envelope into said bulb chassis, an electrically conductive first contact ring positioned over said bulb chassis, an electrically conductive second contact ring positioned over said bulb chassis, electrical insulating means intermediate said first and second electrical contact rings, one of said filament contact legs being in engagement with said first contact ring, the other said filament contact leg being in engagement with said second contact ring, said second ring being in electrical contact with said sleeve, said first contact ring having an exterior diameter smaller than the exterior diameter of said second contact ring and being in engagement with said movable contact means, such that engagement of said movable contact means with said first contact ring completes an electrical circuit to the bulb and positively retains said bulb in said sleeve.

* * * * *